(12) United States Patent
Burstein

(10) Patent No.: US 6,730,128 B2
(45) Date of Patent: May 4, 2004

(54) PROSTHETIC KNEE JOINT

(75) Inventor: Albert H. Burstein, Sarasota, FL (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 10/123,855

(22) Filed: Apr. 16, 2002

(65) Prior Publication Data

US 2003/0023314 A1 Jan. 30, 2003

Related U.S. Application Data

(60) Provisional application No. 60/284,154, filed on Apr. 17, 2001.

(51) Int. Cl.⁷ .................................................. A61F 2/38
(52) U.S. Cl. ................................ 623/20.27; 623/20.31
(58) Field of Search ..................... 623/20.27, 20.14, 623/20.28, 20.31

(56) References Cited

U.S. PATENT DOCUMENTS

| | | | | |
|---|---|---|---|---|
| 4,298,992 A | * | 11/1981 | Burstein et al. | ......... 623/20.27 |
| 4,822,365 A | * | 4/1989 | Walker et al. | ............... 128/898 |
| 5,282,868 A | * | 2/1994 | Bahler | ...................... 623/20.29 |
| 5,702,458 A | * | 12/1997 | Burstein et al. | ......... 623/20.31 |
| 6,406,497 B2 | * | 6/2002 | Takei | ...................... 623/20.31 |

* cited by examiner

*Primary Examiner*—Corrine McDermott
*Assistant Examiner*—Thomas J Sweet
(74) *Attorney, Agent, or Firm*—Greenberg Traurig, LLP

(57) ABSTRACT

The present invention is directed to prosthetic knee joints having femoral and tibial components. More particularly, in one embodiment the knee joint prosthesis of the present invention includes an auxiliary pair of load bearing surfaces in addition to other load bearing surfaces of the tibial and femoral components, which are the medial tibial and femoral condyles, the lateral tibial and femoral condyles, and the central tibial and femoral cam surfaces. The auxiliary pair of load bearing surfaces are located on the tibial component, posterior (i.e, on the rear side of the knee joint) to the central cam, centered between the tibial condyles, and on the femoral component, posterior to the femoral central camming surface, centered between the femoral condyles.

32 Claims, 3 Drawing Sheets

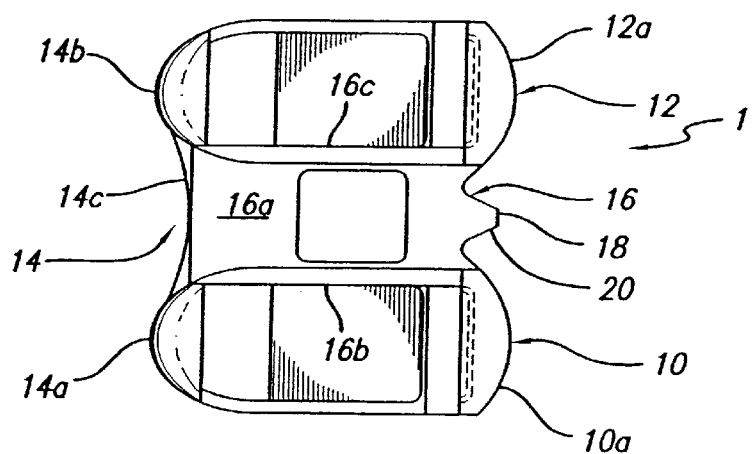
FIG. 1
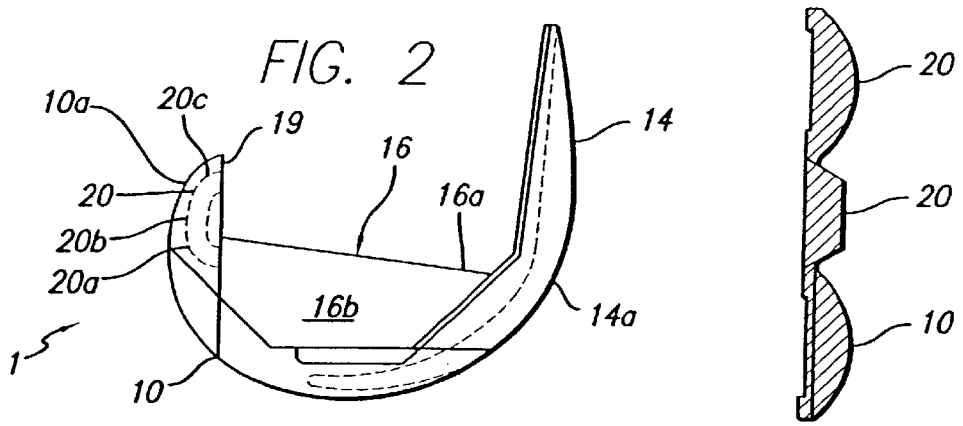
FIG. 2
FIG. 7
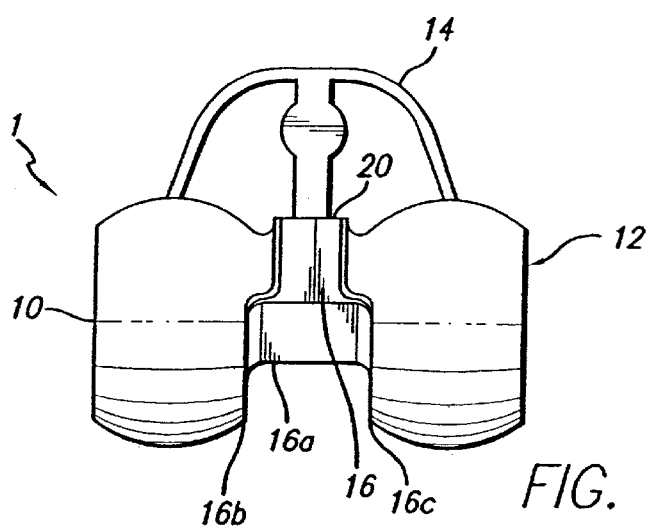
FIG. 3

FIG. 4
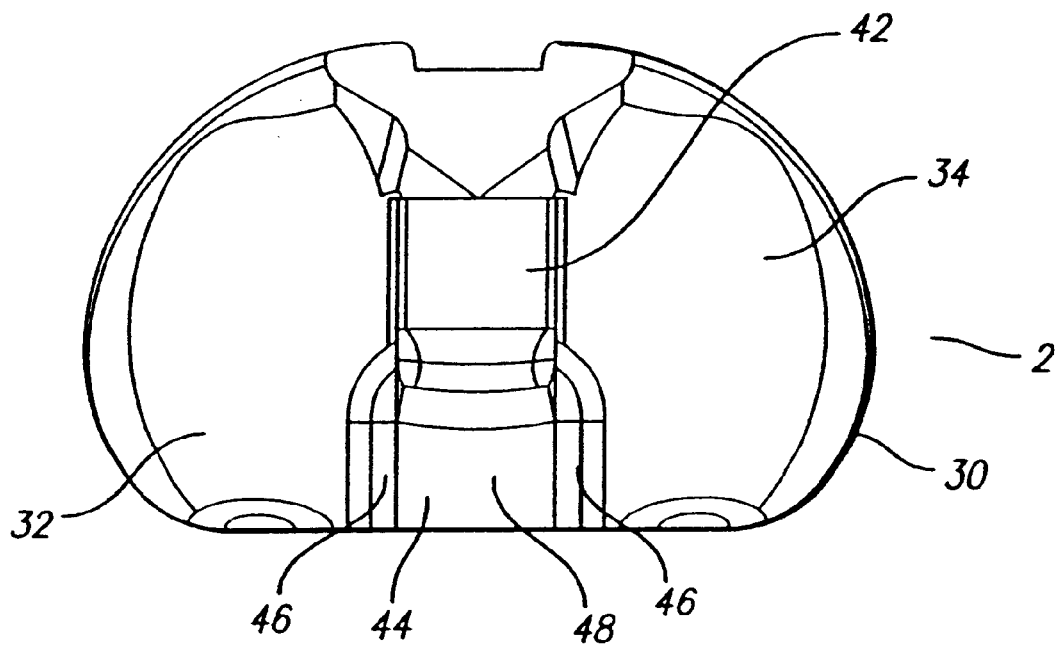
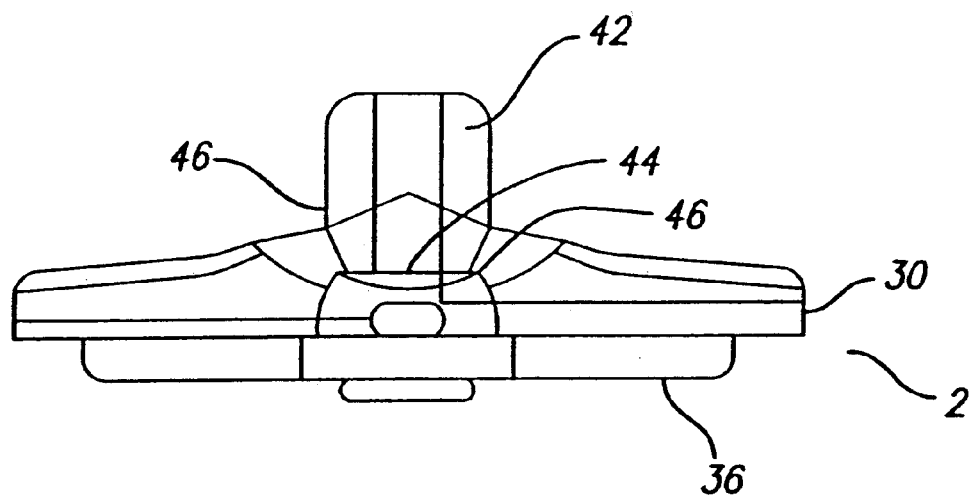
FIG. 6

PROSTHETIC KNEE JOINT

RELATED APPLICATION

This application claims the benefit under 35 U.S.C. 119(e) of U.S. Provisional Application Serial No. 60/284,154, filed Apr. 17, 2001.

FIELD OF THE INVENTION

The present invention is directed to prosthetic knee joints having femoral and tibial components.

BACKGROUND OF THE INVENTION

Prosthetic knee joints have been disclosed in U.S. Pat. Nos. 4,298,992 and 5,702,458, on which the present inventor is named as a co-inventor.

SUMMARY OF THE INVENTION

The present invention is directed to a prosthetic knee joint which offers a greater degree of knee flexion over that which was available with prior art prostheses. This can be accomplished by placing the contact point between the tibial component and the femoral component proximate the posterior edge of the tibial component at the time that the femur, and hence the femoral component, is flexed to the highest possible angle of flexion. However, in providing for the highest possible angle of flexion, by positioning the contact point between the tibial component and the femoral component proximate the posterior edge of the tibial component, there is a possibility that mechanical function of the prosthesis may be compromised. The contact area between the femoral and tibial condyles may be diminished, thus increasing contact stress, and possibly joint wear. Also, at extreme flexion, the femoral component, at either the medial or lateral femoral condyle (or both), may lose contact with its tibial counterpart. This condition could occur if there is rotation of the tibia and femur relative to the other, in which case edge loading of the posterior edge of the load bearing tibial condyle might occur.

The knee joint prosthesis of the present invention includes an auxiliary pair of load bearing surfaces in addition to other load bearing surfaces of the tibial and femoral components, which are the medial tibial and femoral condyles, the lateral tibial and femoral condyles, and the central tibial and femoral cam surfaces. The auxiliary pair of load bearing surfaces are located, on the tibial component, posterior (i.e., on the rear side of the knee joint) to the central cam, centered between the tibial condyles, and on the femoral component, posterior to the femoral central camming surface, centered between the femoral condyles.

It is contemplated that under normal mechanical operation of the knee joint prosthesis of the present invention, that is, with an absence of surface wear or deformation and no rotation at high flexion angles (i.e., greater than 120 degrees, preferably greater than 125 degrees), the auxiliary load bearing surfaces will not transmit loads, or will transmit only a minimal load. However, when wear occurs to an appreciable degree, or where there is internal/external rotation between the tibial and femoral components at high flexion angles, the tibial and femoral auxiliary load bearing surfaces come into contact with each other, transmitting a load in order to stabilize the joint.

If the knee is moved to a high flexion angle, and then experiences rotation between the femur and tibia, the movement of one femoral condyle off of the posterior edge of the corresponding tibial condyle results in contact and load bearing between the auxiliary load bearing surface pair. This prevents excessive vargus/valgus joint motion, thus stabilizing the knee joint and effectively transmitting the joint load.

The relatively smaller contact surface experienced by the knee joint at high flexion angles may result in joint surface wear or cold flow of the joint surfaces. This can produce a decrease of bearing thickness. If the thickness of the medial or lateral tibial condyles decreases, then the auxiliary bearing surface pair would come into contact and transmit a portion of the joint load.

The auxiliary surface of the femoral cam may also increase the "jumping height" of the femur with respect to the tibia. Jumping height is the term used to describe the amount of separation required between the normally contacting tibia and femur that would allow the femur to move forward and jump over the tibial cam. This occurrence, called dislocation, is undesirable. Therefore, maximization of jumping height is desirable in order to prevent dislocation at high flexion angles. Since, during high angles of flexion, the auxiliary load bearing surface of the femoral cam remains proximally within the posterior boundaries of the articulating surfaces of the components, jumping height is maximized.

BRIEF DESCRIPTION OF THE DRAWINGS

FIGS. 1, 2 and 3, are top plan, side elevational, and rear elevational views, respectively, of the femoral component;

FIGS. 4, 5 and 6 are top plan, side elevational, and rear elevational views and cross sectional views of the tibial component; and FIG. 7 is a top plan view of the condyles and cam follower of the femoral component.

DETAILED DESCRIPTION OF THE EMBODIMENT

Figure 5A:
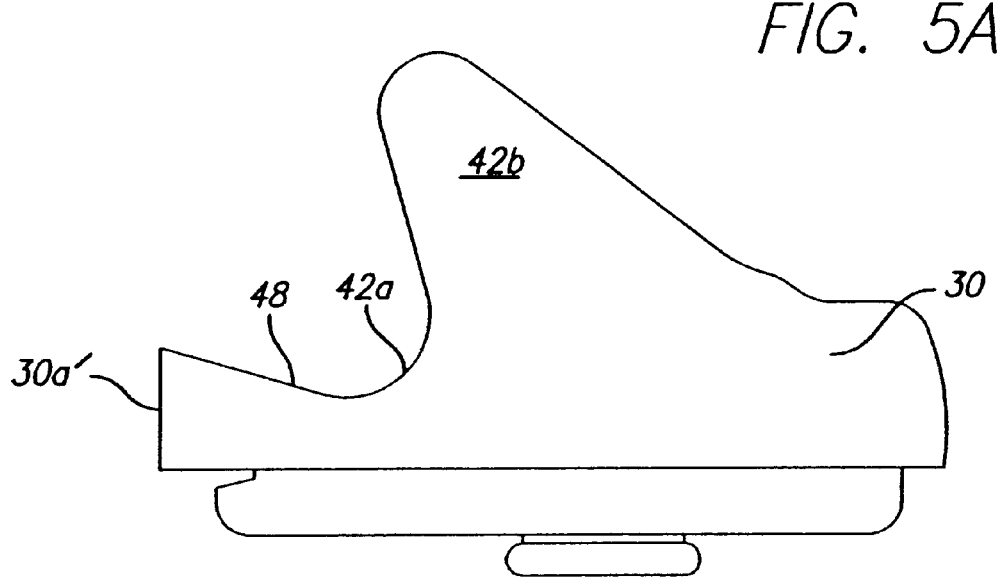

The femoral component comprises a pair of identical laterally spaced-apart femoral condylar portions 10 and 12, each of which is smoothly convexly curved in lateral profile generally to approximate the curvature of an anatomical femoral condyle and is medially laterally convexly curved entirely along its antero-posterior extent. The anterior parts of the condylar portions merge smoothly with convexly curved lateral portions 14a and 14b of a patellar portion 14, the midportion 14c of which is concave and convex and intersects at its inferior extremity a superior wall or roof 16a of a box-like intercondylar portion 16 which, together with patellar portion 14, connects the condylar portions. A pair of laterally spaced-apart side walls 16b and 16c of the recess join the edges of the roof 16a to the internal edges of the condylar portions. An optional opening 18 in the roof 16a of the intercondylar portion 16 allows access to the bone tissue and provides for better integration of the component with anatomical structures and systems.

The surfaces of the femoral component which face the femur are generally flat and, in the case of the "facets" of each the condylar portions 10 and 12, may be bounded by a small rib or flange, thus to provide a keying effect which holds the component securely on the cement used to attach the component to the femur. This pocketed feature also allows for beads or other biological attachment surfaces.

The roof 16a of the intercondylar recess 16 is generally flat (though it does have a slight break between two flat surfaces) and, is generally horizontal (parallel to a nominal base plane). The cam follower surface 20 is located adjacent the recess 16 at the posterior side of the femoral component 1. The cam follower surface 20 is positioned between the condylar portions 10 and 12. From the underside of recess 16, cam follower surface is provided with a curved surface 20a that merges with a substantially flat portion 20b which then curves inward at 20c to merge with upper recess surface 19. The cam follower surface may be dimensioned so that it extends slightly greater in the posterior direction in the vicinity of lower curved surface 20a when compared to the degree it extends in the vicinity of the upper curved surface 20c, as shown in FIG. 2.

The femoral component is preferably made of a surgical grade, durable metal, such as a 316L stainless steel or a chrome-cobalt-molybdenum alloy meeting ASTM Standard #F75. It can also be made of biocompatible polymers. All surfaces which are external to the bone are highly polished. The femoral component can be symmetrical about a vertical antero-posterior center plane, so it can be used on either knee. It also can be asymmetrical (i.e., right or left knee specific).

Figure 5B:
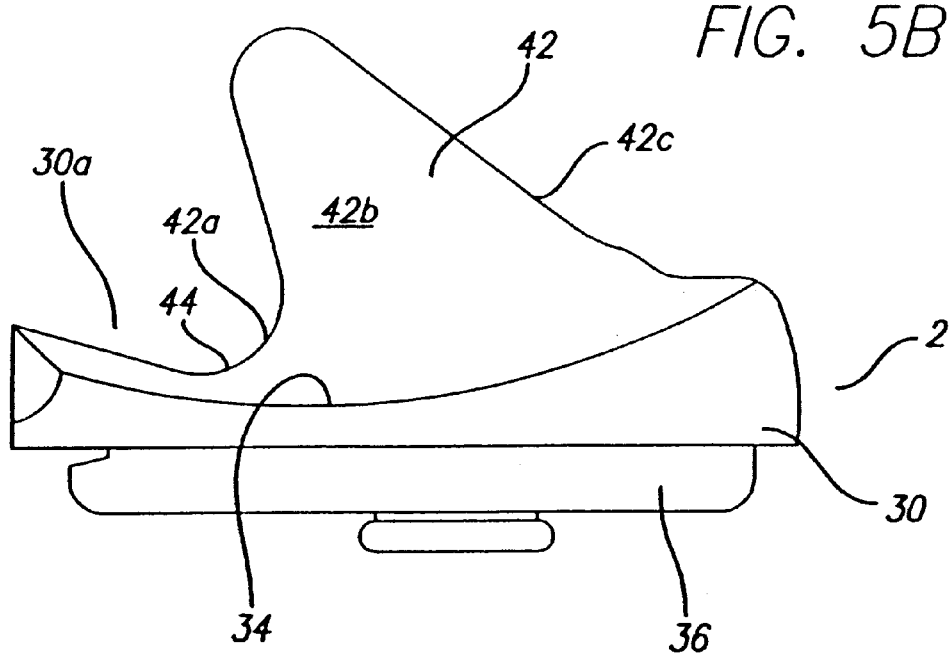

The tibial component 2 (FIGS. 4 to 6) is preferably made of a surgical grade, low-friction, high density, low wearing plastic, such as GUR4150 GUR4120 or other resins known to be suited for these applications. The tibial is also symmetrical about a vertical antero-posterior center plane for right or left use. It comprises an oblong, rounded, disc-like plateau portion 30, the upper surface of which may be flat. A pair of laterally spaced-apart, oblong concavities 32 and 34 receives each of one of the femoral condylar portions. The "nested" support of the femoral component stabilizes the prosthetic joint but still permits antero-posterior translation, lateral angulation and rotation, all of which are involved in normal function of the anatomical knee joint. The lateral curvature is slightly greater than the lateral curvature of the femoral condylar portions.

A base-like fixation portion 36 extends from the bottom surface of the plateau portion 30 to allow attachment to a metal tibial tray for fixation to a tibia in a known manner.

A stabilizing post 42 extends upward from the plateau portion 30 between the concavities 32, 34 and is positioned to be received in the intercondylar recess 16 when the components are assembled. The post 42 is generally triangular in lateral profile and has flat, parallel side surfaces 42b, a concave cam surface 42a at the inferior part of the posterior surface, and an anterior surface which slopes anteriorly and superiorly at an acute angle to a nominal reference plane perpendicular to the nominal axis of the extended leg. The side surfaces of the stabilizing post 42 are in sufficient clearance from the lateral walls of the femoral intercondylar recess to allow normal lateral angulation and rotation of the prosthetic knee joint.

Tibial component 2 is further provided with a surface 44 located in the posterior region of the component, adjacent the stabilizing post 42 and adjacent the cam surface 42a. The surface 44 is centered between the tibial condyles 32 and 34. Sidewalls 46 define the lateral edges of the surface 44. Surface 44 slopes upward from a lower region adjacent the cam surface 42a to an upper region located at the edge 30a' of the posterior surface of the tibial component. See FIG. 5a.

The auxiliary pair of load bearing surfaces of the present invention includes the cam follower 20 and the surface 44. As the femoral condyle portions 10 and 12 rotate through the concavities 32 and 34, the cam following surface 20 becomes engaged with the concave cam surface 42a. As the degree of flexion increases, the upper surface of the femoral condyle portions 10a, 12a begin to become engaged with the concavities 32 and 34. The lower curved portion of cam following surface 20a remains engaged with the cam surface 42a, while a gap is present between the flat portion 20b of cam following surface and the surface 44. However, these surfaces may come in close proximity to each other. Preferably, the size of the gap is 0.01 to 0.4 millimeters under normal mechanical conditions. (Some contact may occur, but is not intended to be load bearing. This arrangement provides for a high degree of flexion in the prosthetic knee joint of the present invention.

Under normal mechanical operation of the knee joint prosthesis of the present invention, that is, with an absence of surface wear or cold flow, and no rotation at high flexion angles (i.e., greater than 120 degrees, preferably greater than 125 degrees), the auxiliary load bearing surfaces will not transmit loads, or will transmit only a minimal load. However, when wear occurs to an appreciable degree, or there is rotation or cold flow between the tibial and femoral components at high flexion angles, the cam following surface 20 and the recess 44 (the femoral and tibial auxiliary load bearing surfaces, respectively) come into contact with each other, transmitting a load in order to stabilize the joint.

If the knee is moved to a high flexion angle, and then experiences rotation between the femur and tibia, the movement of one femoral condyle (e.g., 10) off of the posterior edge of the corresponding tibial concavity (e.g., 32) results in contact and load bearing between the auxiliary load bearing surface pair 20 and 44. This prevents vargus/valgus joint motion, thus stabilizing the knee joint and effectively transmitting the joint load.

The relatively smaller contact surface experienced by the knee joint at high flexion angles may result in joint surface wear or cold flow of the joint surfaces. This can produce a decrease of bearing thickness. If the thickness of the medial or lateral tibial condyles decreases, then the auxiliary bearing surface pair would come into contact and transmit a portion of the joint load.

The auxiliary surface of the femoral cam may also increase the "jumping height" of the femur with respect to the tibia. Jumping height is the term used to describe the amount of separation required between the normally contacting tibia and femur that would allow the femur to move forward and jump over the tibial cam. This occurrence, called dislocation, is undesirable. Therefore, maximization of jumping height is desirable in order to prevent dislocation at high flexion angles. Since, during high angles of flexion, the auxiliary load bearing surface of the femoral cam (cam follower 20) remains proximally within the posterior boundaries of the articulating surfaces of the components, jumping height is maximized.

I claim:

1. A knee joint prosthesis, comprising:
a femoral component having an anterior side and a posterior side, the femoral component including a pair of laterally spaced condylar portions, each of which has a surface which is smoothly convexly curved antero-posteriorly to match generally the lateral profile of an anatomical femoral condyle and smoothly convexly curved laterally throughout its antero-posterior extent, and an intercondylar recess joining the condylar portions;
a cam follower surface located adjacent the recess on the posterior side of the femoral component between the condylar portions, the cam follower surface dimensioned to extend greater in the posterior direction in a lower cam follower surface region when compared to an upper cam follower surface region;

a tibial component having an anterior side and a posterior side, the tibial component including a platform having on its upper surface first and second laterally spaced concavities, each is adapted to receive, in complementary relationship, one of the condylar portions of the femoral component, a tibial post extending up from the platform, the tibial post positioned between the concavities, for reception in the intercondylar recess of the femoral component and having a concavely curved cam surface at a lower end thereof; a tibial auxiliary load bearing surface positioned posterior to the cam surface between the first and second concavities, the tibial auxiliary load bearing surface being adjacent the cam surface; the tibial auxiliary load bearing surface having a profile complementary to the profile of the cam follower surface;

wherein, upon assembly of the knee joint prosthesis, the laterally spaced condylar portions of the femoral component are positioned on the first and second concavities of the tibial component in an arrangement that allows for rotation of the femoral component relative to the tibial component;

wherein, during rotation of the femoral component in normal mechanical operation of the knee joint prosthesis, the cam follower surface engages the cam surface and the cam follower surface does not transmit a joint stabilizing load to the tibial auxiliary load bearing surface; and wherein, when the femoral component rotates at an angle representing a high degree of flexion in normal mechanical operation of the knee joint prosthesis, a gap is present between the cam follower surface and the tibial auxiliary load bearing surface.

2. The knee joint prosthesis of claim 1 wherein the cam follower surface is provided with a curved surface at the lower cam follower surface region that merges with a substantially flat portion, the flat portion merging with a curved surface at the upper cam follower surface region.

3. The knee joint prosthesis of claim 1 wherein, when the femoral component rotates at an angle representing a high degree of flexion in normal mechanical operation of the knee joint prosthesis, the gap has a size from about 0.01 to 0.4 millimeters.

4. The knee joint prosthesis of claim 1 wherein the tibial auxiliary load bearing surface merges with the cam surface.

5. The knee joint prosthesis of claim 1 wherein the tibial auxiliary load bearing surface has sidewalls defining the lateral edges of the tibial auxiliary load bearing surface, and the tibial auxiliary load bearing surface has an upward slope from a region adjacent the cam surface to an upper region located at an edge of the posterior surface of the tibial component.

6. The knee joint prosthesis of claim 1 wherein, when the femoral component rotates at high flexion angles under a condition of tibial component surface wear, cold flow, or rotation between the patient's femur and tibia, the cam follower surface and the tibial auxiliary load bearing surface contact each other in a load bearing relationship.

7. A knee joint prosthesis, comprising:

a femoral component having an anterior side and a posterior side, the femoral component including a pair of laterally spaced condylar portions, each of which has a surface which is convexly curved antero-posteriorly to match generally the lateral profile of an anatomical femoral condyle and convexly curved laterally throughout its antero-posterior extent, and an intercondylar recess joining the condylar portions;

a cam follower surface located adjacent the recess on the posterior side of the femoral component between the condylar portions, the cam follower surface provided with a curved surface at the lower cam follower surface region that merges with a substantially flat portion, the flat portion merging with a curved surface at the upper cam follower surface region, the cam follower surface dimensioned to extend greater in the posterior direction in a lower cam follower surface region when compared to an upper cam follower surface region;

a tibial component having an anterior side and a posterior side, the tibial component including a platform having on its upper surface first and second laterally spaced concavities, each is adapted to receive one of the condylar portions of the femoral component, a tibial post for reception in the intercondylar recess of the femoral component and having a cam surface at a lower end thereof; a tibial auxiliary load bearing surface positioned posterior to the cam surface between the first and second concavities, the tibial auxiliary load bearing surface being adjacent the cam surface; the tibial auxiliary load bearing surface having a profile complementary to the profile of the cam follower surface;

wherein, upon assembly of the knee joint prosthesis, the laterally spaced condylar portions of the femoral component are positioned on the first and second concavities of the tibial component in an arrangement that allows for rotation of the femoral component relative to the tibial component;

wherein, during rotation of the femoral component in normal mechanical operation of the knee joint prosthesis, the cam follower surface engages the cam surface and the cam follower surface does not transmit a joint stabilizing load to the tibial auxiliary load bearing surface; and wherein, when the femoral component rotates at an angle representing a high degree of flexion in normal mechanical operation of the knee joint prosthesis, a gap is present between the cam follower surface and the tibial auxiliary load bearing surface.

8. The knee joint prosthesis of claim 7 wherein, when the femoral component rotates at an angle representing a high degree of flexion in normal mechanical operation of the knee joint prosthesis, the gap has a size from about 0.01 to 0.4 millimeters.

9. The knee joint prosthesis of claim 7 wherein the tibial auxiliary load bearing surface merges with the cam surface.

10. The knee joint prosthesis of claim 7 wherein the tibial auxiliary load bearing surface has sidewalls defining the lateral edges of the tibial load bearing surface, and the tibial load bearing surface has an upward slope from a region adjacent the cam surface to an upper region located at an edge of the posterior surface of the tibial component.

11. The knee joint prosthesis of claim 7 wherein, when the femoral component rotates at high flexion angles under a condition of tibial component surface wear, cold flow, or rotation between the patient's femur and tibia, the cam follower surface and the tibial auxiliary load bearing surface contact each other in a load bearing relationship.

12. A knee joint prosthesis, comprising:

a femoral component having an anterior side and a posterior side, the femoral component including a pair of laterally spaced condylar portions, each of which has a surface which is convexly curved antero-posteriorly to match generally the lateral profile of an anatomical femoral condyle and convexly curved laterally throughout its antero-posterior extent, and an intercondylar recess joining the condylar portions;

a cam follower surface located adjacent the recess on the posterior side of the femoral component between the condylar portions, the cam follower surface dimensioned to extend greater in the posterior direction in a lower cam follower surface region when compared to an upper cam follower surface region;

a tibial component having an anterior side and a posterior side, the tibial component including a platform having on its upper surface first and second laterally spaced concavities, each adapted to receive one of the condylar portions of the femoral component, a tibial post for reception in the intercondylar recess of the femoral component and having a cam surface at a lower end thereof; a tibial auxiliary load bearing surface positioned posterior to the cam surface between the first and second concavities, the tibial auxiliary load bearing surface being adjacent the cam surface; the tibial auxiliary load bearing surface having a profile complementary to the profile of the cam follower surface;

wherein, upon assembly of the knee joint prosthesis, the laterally spaced condylar portions of the femoral component are positioned on the first and second concavities of the tibial component in an arrangement that allows for rotation of the femoral component relative to the tibial component, and when the femoral component rotates at an angle representing a high degree of flexion in normal mechanical operation of the knee joint prosthesis, a gap is present between the cam follower surface and the tibial auxiliary load bearing surface; and wherein, during rotation of the femoral component in normal mechanical operation of the knee joint prosthesis, the cam follower surface engages the cam surface and the cam follower surface does not transmit a joint stabilizing load to the tibial auxiliary load bearing surface.

13. The knee joint prosthesis of claim 12 wherein the cam follower surface is provided with a curved surface at the lower cam follower surface region that merges with a substantially flat portion, the flat portion merging with a curved surface at the upper cam follower surface region.

14. The knee joint prosthesis of claim 12 wherein, when the femoral component rotates at an angle representing a high degree of flexion in normal mechanical operation of the knee joint prosthesis, the gap has a size from about 0.01 to 0.4 millimeters.

15. The knee joint prosthesis of claim 12 wherein the tibial auxiliary load bearing surface has sidewalls defining the lateral edges of the tibial auxiliary load bearing surface, and the tibial auxiliary load bearing surface has an upward slope from a region adjacent the cam surface to an upper region located at an edge of the posterior surface of the tibial component.

16. The knee joint prosthesis of claim 12 wherein the tibial auxiliary load bearing surface merges with the cam surface.

17. The knee joint prosthesis of claim 12 wherein, when the femoral component rotates at high flexion angles under a condition of tibial component surface wear, cold flow, or rotation between the patient's femur and tibia, the cam follower surface and the tibial auxiliary load bearing surface contact each other in a load bearing relationship.

18. A knee joint prosthesis, comprising:

a femoral component having an anterior side and a posterior side, the femoral component including a pair of laterally spaced condylar portions, each of which has a surface which is convexly curved antero-posteriorly to match generally the lateral profile of an anatomical femoral condyle and convexly curved laterally throughout its antero-posterior extent, and an intercondylar recess joining the condylar portions;

a cam follower surface located adjacent the recess on the posterior side of the femoral component between the condylar portions, the cam follower surface dimensioned to extend greater in the posterior direction in a lower cam follower surface region when compared to an upper cam follower surface region;

a tibial component having an anterior side and a posterior side, the tibial component including a platform having on its upper surface first and second laterally spaced concavities, each is adapted to receive one of the condylar portions of the femoral component, a tibial post for reception in the intercondylar recess of the femoral component and having a cam surface at a lower end thereof; a tibial auxiliary load bearing surface positioned posterior to the cam surface between the first and second concavities, the tibial auxiliary load bearing surface being adjacent the cam surface; the tibial auxiliary load bearing surface having a profile complementary to the profile of the cam follower surface;

wherein, upon assembly of the knee joint prosthesis, the laterally spaced condylar portions of the femoral component are positioned on the first and second concavities of the tibial component in an arrangement that allows for rotation of the femoral component relative to the tibial component;

wherein, when the femoral component rotates at an angle representing a high degree of flexion in normal mechanical operation of the knee joint prosthesis, a gap is present between the cam follower surface and the tibial auxiliary load bearing surface, the gap having a size from about 0.01 to 0.4 millimeters; and wherein, during rotation of the femoral component in normal mechanical operation of the knee joint prosthesis, the cam follower surface engages the cam surface and the cam follower surface does not transmit a joint stabilizing load to the tibial auxiliary load bearing surface.

19. The knee joint prosthesis of claim 18 wherein the cam follower surface is provided with a curved surface at the lower cam follower surface region that merges with a substantially flat portion, the flat portion merging with a curved surface at the upper cam follower surface region.

20. The knee joint prosthesis of claim 18 wherein the tibial auxiliary load bearing surface has sidewalls defining the lateral edges of the tibial auxiliary load bearing surface, and the tibial auxiliary load bearing surface has an upward slope from a region adjacent the cam surface to an upper region located at an edge of the posterior surface of the tibial component.

21. The knee joint prosthesis of claim 18 wherein the tibial auxiliary load bearing surface merges with the cam surface.

22. The knee joint prosthesis of claim 18 wherein, when the femoral component rotates at high flexion angles under a condition of tibial component surface wear, cold flow, or rotation between the patient's femur and tibia, the cam follower surface and the tibial auxiliary load bearing surface contact each other in a load bearing relationship.

23. A knee joint prosthesis, comprising:

a femoral component having an anterior side and a posterior side, the femoral component including a pair of laterally spaced condylar portions, each of which has a surface which is convexly curved antero-posteriorly to match generally the lateral profile of an anatomical femoral condyle and convexly curved laterally throughout its antero-posterior extent, and an intercondylar recess joining the condylar portions;

a cam follower surface located adjacent the recess on the posterior side of the femoral component between the condylar portions, the cam follower surface dimensioned to extend greater in the posterior direction in a lower cam follower surface region when compared to an upper cam follower surface region;

a tibial component having an anterior side and a posterior side, the tibial component including a platform having on its upper surface first and second laterally spaced concavities, each adapted to receive one of the condylar portions of the femoral component, a tibial post for reception in the intercondylar recess of the femoral component and having a cam surface at a lower end thereof; a tibial auxiliary load bearing surface positioned posterior to the cam surface between the first and second concavities, the tibial auxiliary load bearing surface merging with the cam surface; the tibial auxiliary load bearing surface having a profile complementary to the profile of the cam follower surface;

wherein, upon assembly of the knee joint prosthesis, the laterally spaced condylar portions of the femoral component are positioned on the first and second concavities of the tibial component in an arrangement that allows for rotation of the femoral component relative to the tibial component;

wherein, during rotation of the femoral component in normal mechanical operation of the knee joint prosthesis, the cam follower surface engages the cam surface and the cam follower surface does not transmit a joint stabilizing load to the tibial auxiliary load bearing surface; and wherein, when the femoral component rotates at an angle representing a high degree of flexion in normal mechanical operation of the knee joint prosthesis, a gap is present between the cam follower surface and the tibial auxiliary load bearing surface.

24. The knee joint prosthesis of claim 23 wherein, when the femoral component rotates at an angle representing a high degree of flexion in normal mechanical operation of the knee joint prosthesis, the gap has a size from about 0.01 to 0.4 millimeters.

25. The knee joint prosthesis of claim 23 wherein the tibial auxiliary load bearing surface has sidewalls defining the lateral edges of the tibial auxiliary load bearing surface, and the tibial auxiliary load bearing surface has an upward slope from a region adjacent the cam surface to an upper region located at an edge of the posterior surface of the tibial component.

26. The knee joint prosthesis of claim 23 wherein the cam follower surface is provided with a curved surface at the lower cam follower surface region that merges with a substantially flat portion, the flat portion merging with a curved surface at the upper cam follower surface region.

27. The knee joint prosthesis of claim 23 wherein, when the femoral component rotates at high flexion angles under a condition of tibial component surface wear, cold flow, or rotation between the patient's femur and tibia, the cam follower surface and the tibial auxiliary load bearing surface contact each other in a load bearing relationship.

28. A knee joint prosthesis, comprising:
a femoral component having an anterior side and a posterior side, the femoral component including a pair of laterally spaced condylar portions, each of which has a surface which is convexly curved antero-posteriorly to match generally the lateral profile of an anatomical femoral condyle and convexly curved laterally throughout its antero-posterior extent, and an intercondylar recess joining the condylar portions;

a cam follower surface located adjacent the recess on the posterior side of the femoral component between the condylar portions, the cam follower surface dimensioned to extend greater in the posterior direction in a lower cam follower surface region when compared to an upper cam follower surface region;

a tibial component having an anterior side and a posterior side, the tibial component, including a platform having on its upper surface first and second laterally spaced concavities, each adapted to receive on of the condylar portions of the femoral component, a tibial post for reception in the intercondylar recess of the formal component and having a cam surface at a lower end thereof; a tibial auxiliary load bearing surface positioned posterior to the cam surface between the first and second concavities, the tibial auxiliary load bearing surface being adjacent the cam surface; the tibial auxiliary load bearing surface having sidewalls defining the lateral edges of the tibial auxiliary load bearing surface, the tibial auxiliary load bearing surface having an upward slop from the region adjacent the cam surface to an upper region located at an edge of the posterior surface of the tibial component;

wherein, upon assembly of the knee joint prosthesis, the laterally spaced condylar portions of the femoral component are positioned on the first and second concavities of the tibial component in an arrangement that allows for rotation of the femoral component relative to the tibial component;

wherein, during rotation of the femoral component in normal mechanical opertion of the knee joint prosthesis, the cam follower surface engages the cam surface and the cam follower surface does not transmit a joint stabilizing load to the tibial auxiliary load bearing surface; and wherein, when the femoral component rotates at an angle representing a high degree of flexion in normal mechanical operation of the knee joint prosthesis, a gap is present between the cam follower surface and the tibial auxiliary load bearing surface.

29. The knee joint prosthesis of claim 28 wherein, when the femoral component rotates at an angle representing a high degree of flexion in normal mechanical opertion of the knee joint prosthesis, the gap has a size from about 0.01 to 0.4 millimeters.

30. The knee joint prosthesis of claim 28 wherein the tibial auxiliary load bearing surface merges with the cam surface.

31. The knee joint prosthesis of claim 28 wherein the cam follower surface is provided with a curved surface at the lower cam follower surface region that merges with a substantially flat portion, the flat portion merging with a curved surface at the upper cam follower surface region.

32. The knee joint prosthesis of claim 28 wherein, when the femoral component rotates at high flexion angles under a condition of tibial component surface wear, cold flow, or rotation between the patient's femur and tibia, the cam follower surface and the tibial auxiliary load bearing surface contact each other in a load bearing relationship.

* * * * *